(12) United States Patent  
Burkholz

(10) Patent No.: US 8,747,333 B2
(45) Date of Patent: Jun. 10, 2014

(54) BLOOD TEST STRIP AND AN INTRAVENOUS CATHETER SYSTEM

(75) Inventor: Jonathan Karl Burkholz, Salt Lake City, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 2 days.

(21) Appl. No.: 13/181,002

(22) Filed: Jul. 12, 2011

(65) Prior Publication Data

US 2012/0016213 A1 Jan. 19, 2012

Related U.S. Application Data

(60) Provisional application No. 61/364,551, filed on Jul. 15, 2010.

(51) Int. Cl.
*A61B 5/00* (2006.01)
*A61B 10/02* (2006.01)

(52) U.S. Cl.
USPC ........... 600/573; 600/576; 600/580; 600/584; 422/68.1

(58) Field of Classification Search
USPC .................. 600/584, 573, 576, 580; 422/68.1
See application file for complete search history.

(56) References Cited

U.S. PATENT DOCUMENTS

| | | | |
|---|---|---|---|
| 3,859,998 A | 1/1975 | Thomas et al. | |
| 4,003,403 A | 1/1977 | Nehring | |
| 4,193,399 A | 3/1980 | Robinson | |
| 4,200,096 A | 4/1980 | Charvin | |
| 4,269,186 A | 5/1981 | Loveless et al. | |
| 4,682,980 A | 7/1987 | Suzuki | |
| 4,765,588 A | 8/1988 | Atkinson | |
| 4,917,671 A | 4/1990 | Chang | |
| 4,935,010 A | 6/1990 | Cox et al. | |
| 5,032,116 A | 7/1991 | Peterson et al. | |
| 5,226,883 A | 7/1993 | Katsaros et al. | |
| 5,242,411 A | 9/1993 | Yamamoto et al. | |
| 5,290,246 A | 3/1994 | Yamamoto et al. | |
| 5,368,029 A | 11/1994 | Holcombe et al. | |
| 5,374,401 A * | 12/1994 | von Berg | 422/534 |
| 5,542,932 A | 8/1996 | Daugherty | |
| 5,730,123 A | 3/1998 | Lorenzen et al. | |
| 5,947,932 A | 9/1999 | Desecki et al. | |
| 6,616,632 B2 * | 9/2003 | Sharp et al. | 604/117 |
| 6,623,702 B2 * | 9/2003 | Allen et al. | 422/547 |
| 6,786,106 B2 * | 9/2004 | Alley | 73/864.51 |
| 6,872,358 B2 * | 3/2005 | Hagen et al. | 422/430 |
| 6,939,450 B2 * | 9/2005 | Karinka et al. | 204/409 |
| 7,299,081 B2 * | 11/2007 | Mace et al. | 600/345 |
| 8,066,670 B2 | 11/2011 | Cluff et al. | |

(Continued)

FOREIGN PATENT DOCUMENTS

| | | | |
|---|---|---|---|
| WO | WO 2004/098685 A1 | 11/2004 | |
| WO | WO 2008/058132 A2 | 5/2008 | |
| WO | WO 2008/058133 A2 | 5/2008 | |

*Primary Examiner* — Sean Dougherty
(74) *Attorney, Agent, or Firm* — Jeanne Lukasavage; Craig Metcalf; Kirton McConkie

(57) ABSTRACT

A blood test strip useful for venting a closed intravenous system and collecting a blood sample is described herein. The blood test strip includes a blood test strip, one or more vents, and a gripping member coupled to the proximal end of the blood test strip. The one or more vents are disposed between the distal and the proximal portions of the blood test strip.

14 Claims, 11 Drawing Sheets

(56) References Cited

U.S. PATENT DOCUMENTS

| | | |
|---|---|---|
| 8,070,725 B2 | 12/2011 | Christensen |
| 8,383,044 B2 * | 2/2013 | Davis et al. .................. 422/68.1 |
| 2002/0046614 A1 * | 4/2002 | Alley ......................... 73/864.91 |
| 2004/0102718 A1 * | 5/2004 | Trudeau et al. ............... 600/584 |
| 2004/0116830 A1 * | 6/2004 | Trudeau et al. ............... 600/584 |
| 2004/0181192 A1 | 9/2004 | Cuppy |
| 2005/0136501 A1 * | 6/2005 | Kuriger ........................... 435/14 |
| 2005/0273019 A1 | 12/2005 | Conway et al. |
| 2005/0277850 A1 * | 12/2005 | Mace et al. ................... 600/584 |
| 2007/0043334 A1 | 2/2007 | Guala |
| 2007/0281321 A1 * | 12/2007 | Nagale et al. .................. 435/7.1 |
| 2008/0045862 A1 * | 2/2008 | Dalebout et al. ............... 600/573 |
| 2008/0255473 A1 | 10/2008 | Dalebout et al. |
| 2008/0287906 A1 | 11/2008 | Burkholz et al. |
| 2009/0099431 A1 | 4/2009 | Dalebout et al. |
| 2009/0215159 A1 * | 8/2009 | Kirby ......................... 435/287.2 |
| 2010/0137778 A1 * | 6/2010 | Kunjan et al. ................. 604/6.15 |
| 2011/0009717 A1 * | 1/2011 | Davis et al. ................... 600/309 |
| 2012/0016265 A1 | 1/2012 | Peterson et al. |
| 2012/0016307 A1 | 1/2012 | Burkholz et al. |

\* cited by examiner

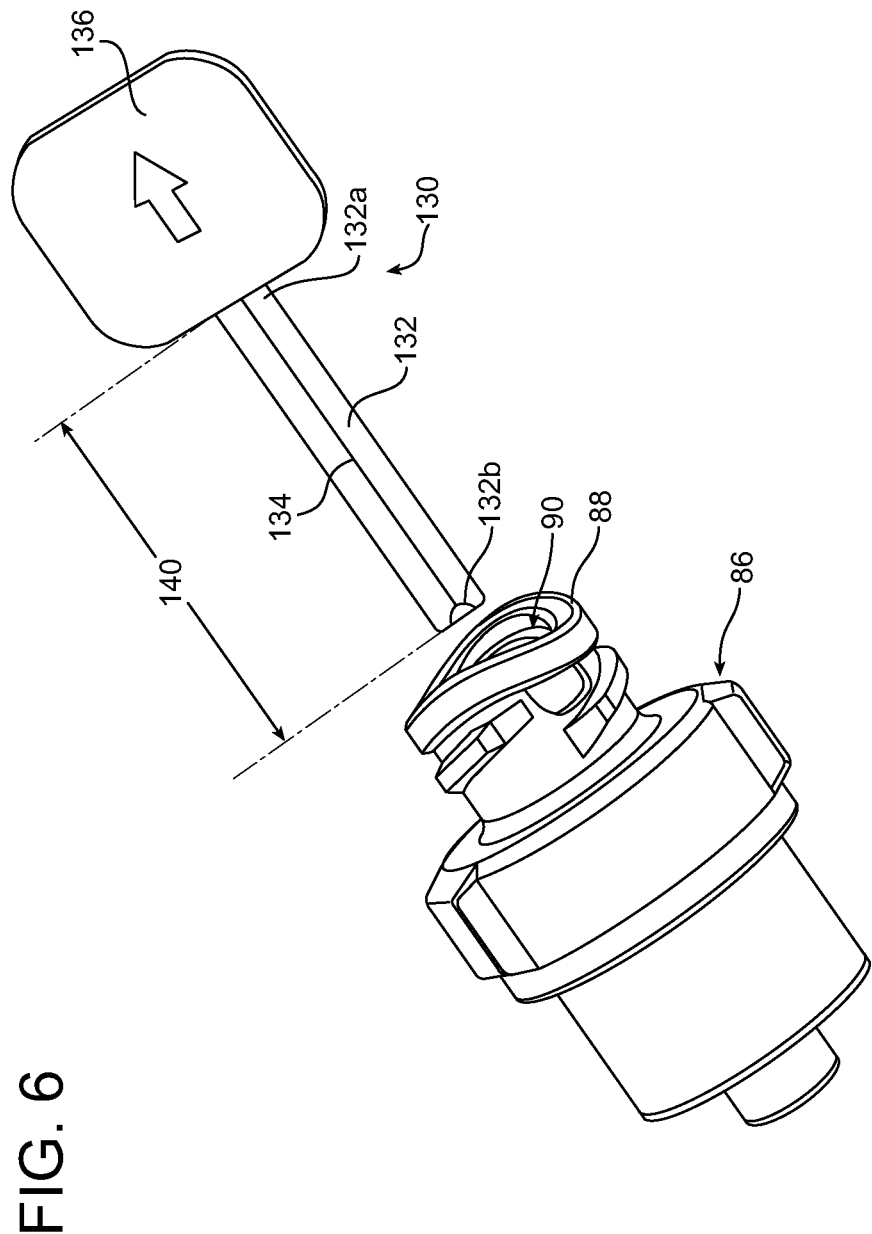

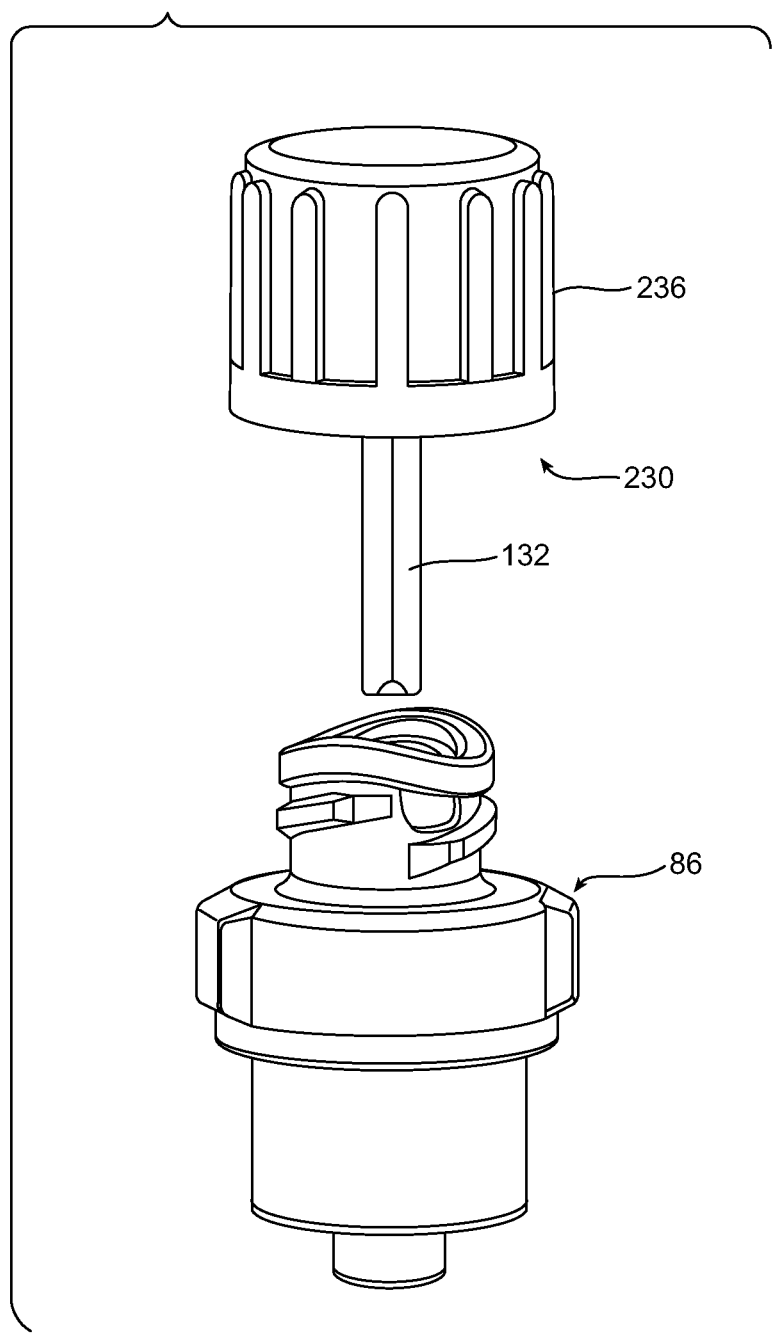

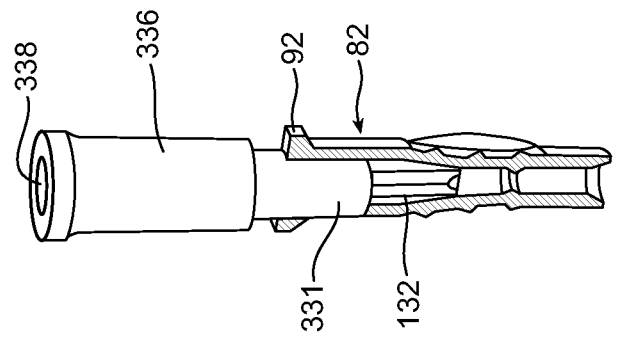
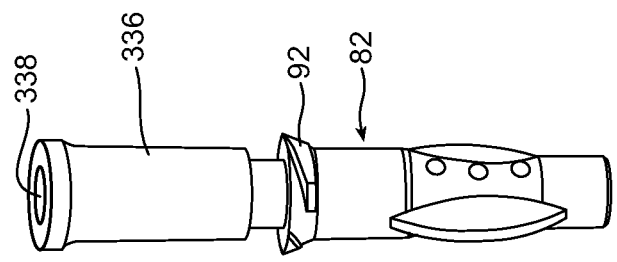
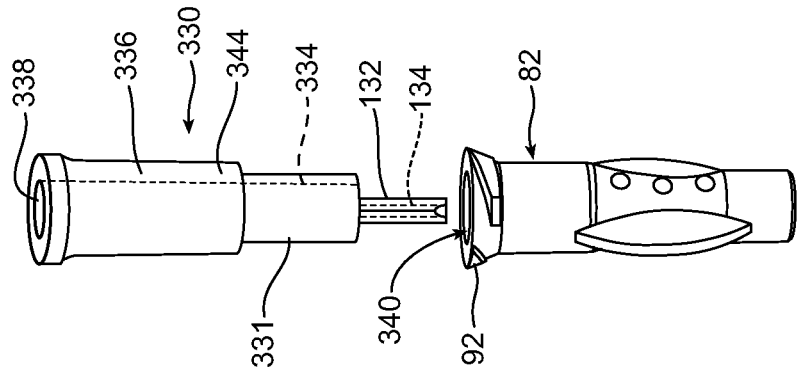

BLOOD TEST STRIP AND AN INTRAVENOUS CATHETER SYSTEM

RELATED APPLICATIONS

This application claims the benefit of U.S. Provisional Application No. 61/364,551, filed Jul. 15, 2010, entitled CLOSED CATHETER SYSTEM VENTING DEVICE WITH INTEGRATED BLOOD SAMPLE TEST STRIP, which is incorporated herein in its entirety.

BACKGROUND

The present disclosure relates to blood testing and blood sampling. Blood sampling is a common health care procedure involving the withdrawal of blood from a patient. Blood samples are commonly taken from hospitalized, homecare, and emergency room patients either by finger stick, heel stick, or venipuncture. Once collected, blood samples are tested to determine the physiological and biochemical states of a patient, such as disease, mineral content, drug effectiveness, and organ function. Blood tests are not commonly performed in the same room, the point of care, as the patient, but are usually performed at remote laboratories.

One common blood test is a test of blood glucose levels in blood. Blood glucose tests can be performed by drawing blood using a finger stick and then collecting the blood into a diagnostic cartridge or container. The diagnostic cartridge is transported to a testing machine or laboratory where the patient's blood glucose level is determined. Other blood tests commonly analyze blood gas electrolyte levels, lithium levels, ionized calcium levels, acute coronary syndrome (ACS) and deep vein thrombosis/pulmonary embolism (DVT/PE).

Blood testing is frequently necessary prior to surgery or other medical procedures. For example, there are indications that diabetes contributes to an increase risk of Surgical Site Infection (SSI). Accordingly some guidelines suggest that diabetes is one characteristic that may influence the development of SSI. As such, preoperative blood glucose control is deemed a possible SSI risk reduction measure. Thus, it can be beneficial to determine blood glucose levels prior to surgery.

Despite advancements in blood testing and diagnostics, blood-sampling techniques have remained relatively unchanged. Blood samples have traditionally been drawn using hypodermic needles, vacuum tubes, or catheter assemblies. In some instances, clinicians have been observed to collect blood from a catheter assembly by inserting a syringe needle through a septum in a catheter assembly and withdrawing blood from a patient through the inserted catheter assembly. These procedures utilize syringe needles and vacuum tubes as intermediate devices from which the collected blood sample is typically withdrawn prior to testing. Such processes are device and time intensive, each device adding to the time and cost of blood testing. Accordingly, there is a need for more efficient blood sampling and testing devices and methods.

SUMMARY

The present invention has been developed in response to problems and needs in the art that have not yet been fully resolved by currently available blood sampling devices and methods. The present invention relates generally to a blood test strip and intravenous (IV) catheter system which provides a point-of-use device that, in a single device, vents an IV system and collects blood on a blood test strip. As such, these devices and systems reduce waste and improve testing and sampling techniques.

In one aspect of the invention, intravenous catheter system comprising an intravenous catheter, an access port coupled to the intravenous catheter, and a venting device. The venting device is shaped and sized to selectively access the port. A proximal portion of the venting device has a gripping member, and distal portion of the venting device has a blood test member.

Implementations may include one or more of the following features. The blood test member may be a blood test strip extending distally from the gripping member. The access port may include a septum, and the blood test strip may be selectively disposed within a slit of the septum. The septum may have a thickness between a proximal side and a distal side of the septum, the one or more vents having a length longer than the septum thickness. The gripping member may be a cap that is shaped and sized to cover the septum. The blood test strip may include one or more reservoirs that collectively retain blood therein when drawn through the slit of the septum. The venting device may include one or more vents extending therethrough. The one or more vents may include at least a hole having dimensions that permit the passage of gas but not blood, a gas permeable membrane, or channel formed on an outer surface of the blood test member having dimensions that permit the passage of gas but not blood. The one or more vents may extend through at least one of the gripping member, the blood test member, and both the gripping member and the blood test member. The access port may include a luer connector, and the gripping member may include a cap that selectively connects to the luer connector. The blood test strip may include at least one diagnostic reagent thereon.

In another aspect, a blood test strip comprises a blood test strip, one or more vents disposed between a distal portion and a proximal portion of the blood test strip, and a gripping member coupled to the proximal end of the blood test strip.

Implementations may include one or more of the following features. The one or more vents may be disposed through the gripping member. The one or more vents may include a hole having dimensions that permit the passage of gas but not blood, a gas permeable membrane, or channel formed on an outer surface of the blood test member having dimensions that permit the passage of gas but not blood. The gripping member may be a cap that is shaped and sized to cover a female luer adapter. The gripping member may be a gripping tab. The blood test strip may include at least one diagnostic reagent thereon.

In another aspect, a method for venting a closed intravenous system and for blood collecting includes the following: Providing a venting device having at least one vent disposed therethrough and having a blood test member. Inserting the blood test member of the venting device at least partially into an access port of the closed intravenous catheter system. Venting gas from the closed intravenous catheter system through at least one vent in the venting device. Withdrawing the blood test member from the access port after the blood test member collects blood from within the closed intravenous catheter system. Implementations of the method may include one or more of the following. Using the blood test member to test the collected blood, and/or venting gas through at least one vent in a blood test strip.

These and other features and advantages of the present invention may be incorporated into certain embodiments of the invention and will become more fully apparent from the following description and appended claims, or may be learned by the practice of the invention as set forth hereinafter. The present invention does not require that all the advantageous features and all the advantages described herein be incorporated into every embodiment of the invention.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. These drawings depict only typical embodiments of the invention and are not therefore to be considered to limit the scope of the invention.

FIG. 6 is a perspective view of a venting device having a blood test strip and a gripping tab as well as a luer connector device, according to some embodiments.

FIG. 8 is a perspective view of a venting device having a blood test strip and a gripping cap as well as a luer access port, according to some embodiments.

FIG. 10 is a perspective view of a venting device having a blood test strip and a gripping member as well as an access port, according to some embodiments.

FIG. 11A is a perspective view of the venting device of FIG. 10 within the access port.

FIG. 11B is a cross-sectional view of the venting device of FIG. 11A within the access port.

DETAILED DESCRIPTION OF THE INVENTION

The presently preferred embodiments of the present invention will be best understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

The present invention relates generally to a blood test strip and intravenous (IV) catheter system that provides a point-of-use device that, in a single device, vents IV systems and collects blood on a blood test strip. As such, these devices and systems reduce waste and improve testing and sampling techniques. Generally, the systems, methods, and devices described herein include a blood test member on a venting device, such as a vent plug. This combination permits both venting and blood sampling to be accomplished simultaneously.

Figure 1:
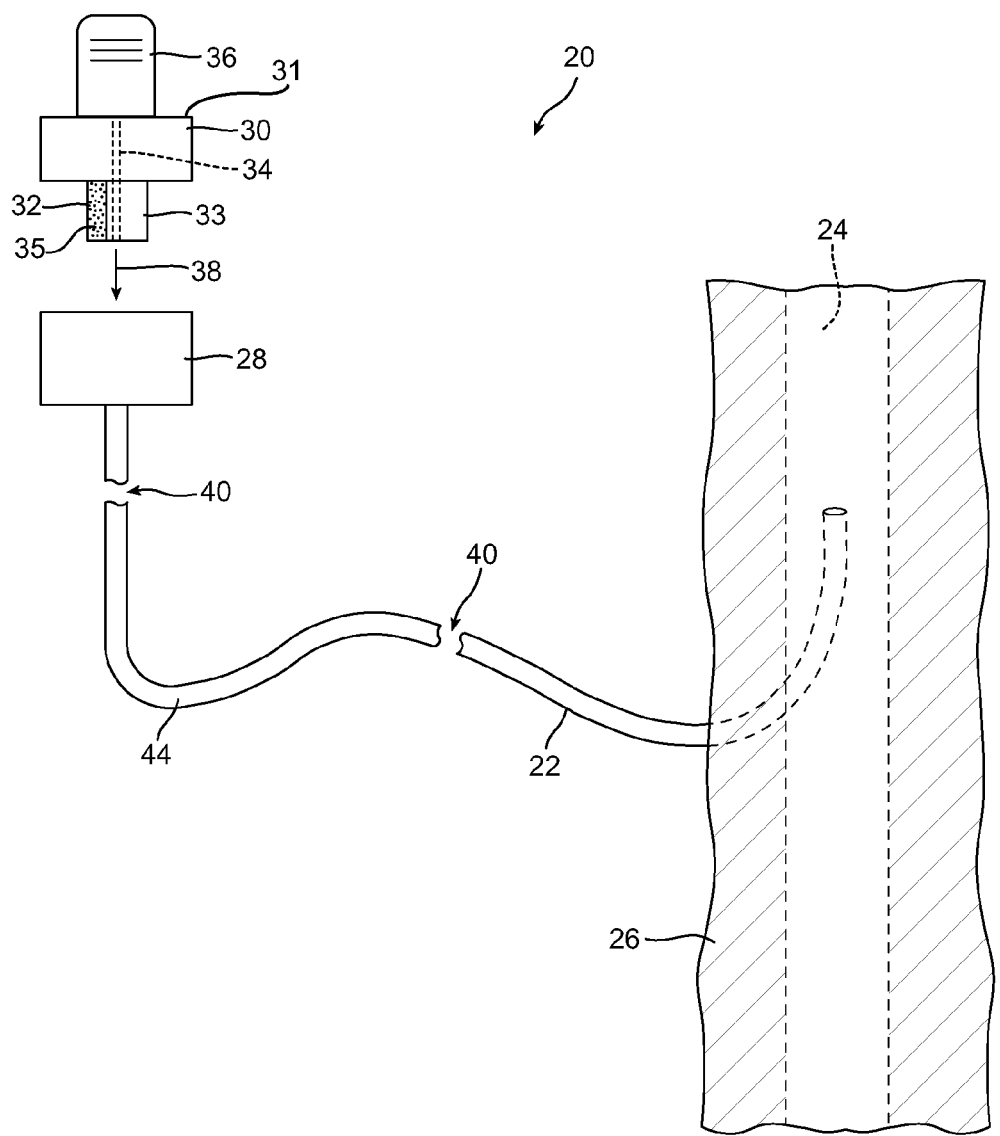
FIG. 1 is a perspective view of an IV system and a venting device prior to insertion into the IV system, according to some embodiments.

FIG. 1 depicts a representative IV system 20 that accesses a patient's blood vessel (such as a vein) 24. This IV system 20 includes access port 28 that is used selectively access the IV system, such as to introduce a substance via an IV tube (or a catheter tube) 22 across the skin 26 and into a blood vessel 24. Access ports can include open and closed ports, including ports that provide selective access to the IV system 20, such as access ports having one or more valves, septa, or other like barriers. Breaks 40 in the IV system 20 indicate that a number of additional components could be, but are not required to be, included at these locations. Examples of such components can include the components depicted in FIG. 5 as well as other components known in the art.

During IV therapy, gas 44 within the system 20 can be vented to eliminate the gas within the catheter system so that it is not introduced into the patient when fluids or medicaments are administered to the patient. Infusion may also allow blood flashback into the system 20 for visual confirmation of proper catheter placement. To vent the gas 44, a venting device 30 is inserted, at least partially, into the access port 28, along the direction of insertion 38. The venting device 30 creates a gas communication channel between the IV system 20 and the external environment, allowing gas 44 within the system to flow therethrough. The gas communication channel can include one or more vents 34 in the venting device 30. As described herein, a vent 34 can be any opening that permits the escape of gas 44 within the system, including a small hole, a channel, or other like formation or device. A vent 34 can also include a filter, such as a gas permeable membrane or other device that restricts the flow of blood therethrough. In some configurations, one or more vents 34 can be located on or through various parts of the venting device 30, including the blood test member 32, the gripping member 36, the main body 31, and a distal body extension 33.

Figure 2:
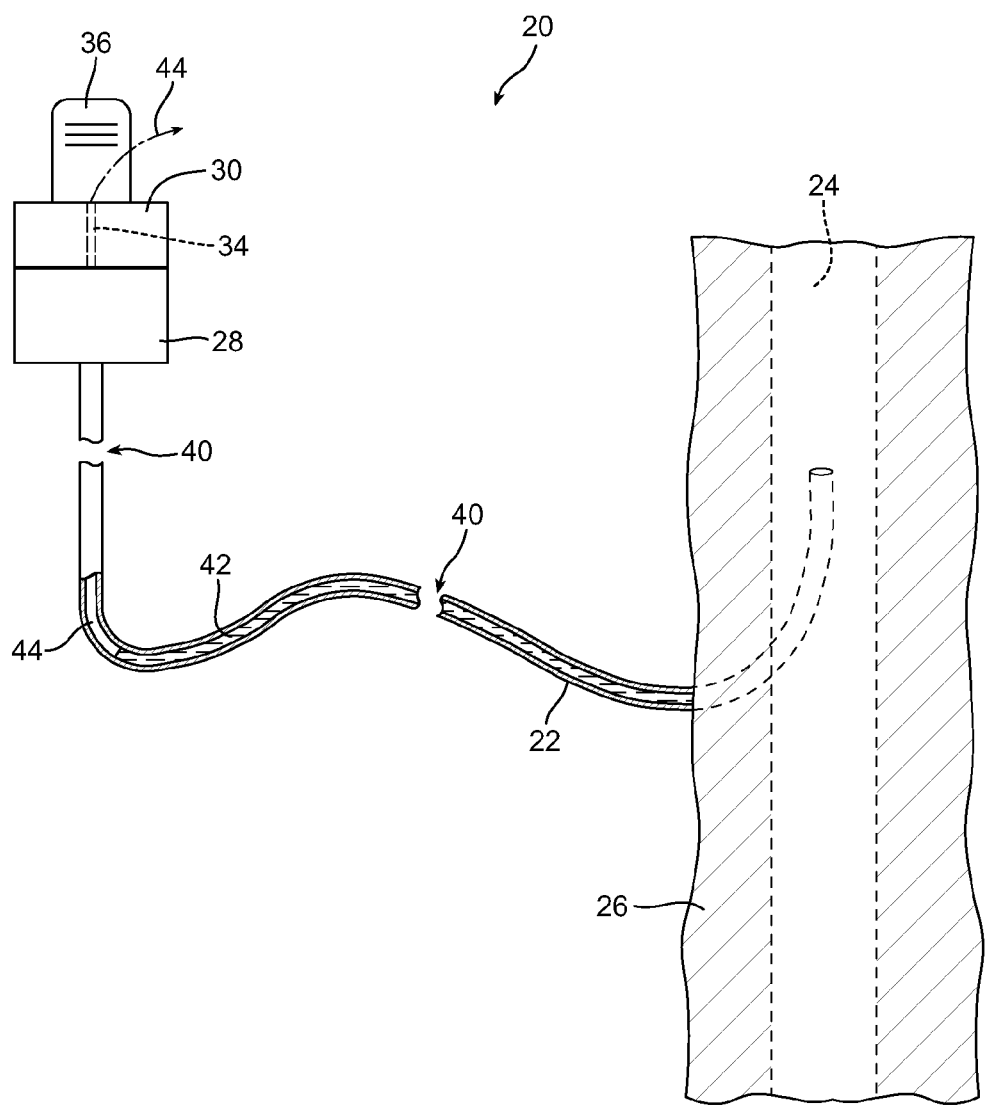
FIG. 2 is a perspective view of the IV system and venting device of FIG. 1 after the venting device has been inserted into the IV system, according to some embodiments.
Figure 3:
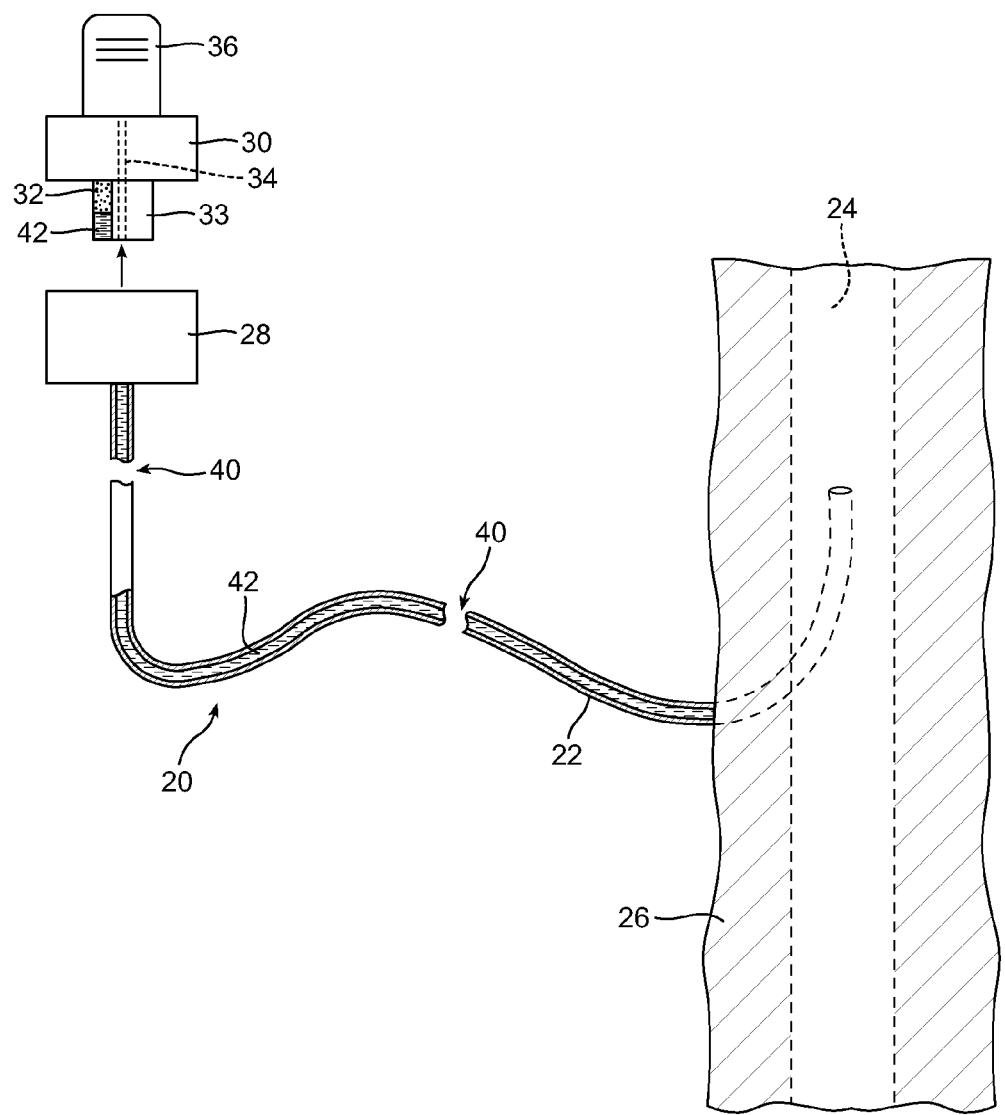
FIG. 3 is a perspective view of the IV system and venting device of FIGS. 1 and 2 after the venting device has been withdrawn from the IV system, according to some embodiments.

As depicted in FIG. 2, in addition to venting gases 44 from the IV system 20, the venting device 30 can collect a blood sample 42 from the blood that fills the IV system 20 during the venting process. During venting, gas 44 exits the IV system 20 and is replaced by blood 42, which enters into the IV system 20 under the pressure of the patient's blood pressure. When venting is complete, as shown in FIG. 3, blood 42 has replaced the gas 44 within the IV system 20. A blood test member 32 within the IV system 20 is thus in contact with blood 42 and collects a sample of blood 42 thereon, which can be removed for testing. A blood test member includes any member or component that is used to collect and test blood in a similar manner to a blood test strip. In some configurations, the blood test member 32 includes a diagnostic component that diagnoses characteristics of the blood and can, in some embodiments, display the results of the diagnosis to the clinician. In other configurations, the blood test member 32 includes electrical contacts (not shown) that are coupled to a separate testing device for testing characteristics of the blood sample, for example, by passing a current therethrough.

The blood test member 32 has structural features and/or properties that enable it to collect a blood sample when inserted into an access port 28. For instance, in some embodiments, the blood test member 32 includes one or more reservoir, shown in FIG. 1 as pores in the blood test member, wherein blood is collected and/or retained. In some instances, the one or more reservoir includes an indentation, a channel, a capillary tube, and/or an absorbent material. In some configurations, the one or more reservoir is configured to retain an adequate amount of blood when the venting device 30 is withdrawn from the access port 28. Generally, an adequate blood sample includes between about 0.1 μL to about 5 mL of blood. In some instances, blood test strips known in the art can be used as a blood test member 32. Such strips can be coupled to the body 31 of the venting device or to the gripping member 36. Such strips can be designed for testing specific blood characteristics, such as blood glucose, red blood cells, white blood cells, a complete blood count, platelets, hemoglobin, hematocrit, calcium, electrolytes, blood urea nitrogen, blood enzymes, cholesterol, etc.

A blood test member 32 can be used with a component of a blood test system or act as a self-contained blood test device. For example, in some embodiments, the blood test member 32 can collect a blood sample and is then inserted into or coupled a blood test device for testing the collected blood. In other embodiments, a collected blood sample reacts with a diagnostic reagent disposed on the blood test member 32 and reacts with the diagnostic reagent to produce visible or non-visible test results. Such results can include a color change, or other such indication.

In some configurations, the venting device 30 includes a gripping member 36, such as a gripping tab or gripping cap that can be gripped by a clinician handling the venting device 30. The gripping member 36 can be positioned on the venting device 30 at a proximal location, away from the blood test member 32, to prevent contact with blood 42 on the venting device 30 and avoid unnecessary contact with the port 28. Once gripped, a clinician can withdraw the venting device 30 from the IV system 20 and maneuver it during subsequent blood testing procedures. In some configurations, the gripping member 36 is made of plastic or another non-absorbent material.

Figure 4:
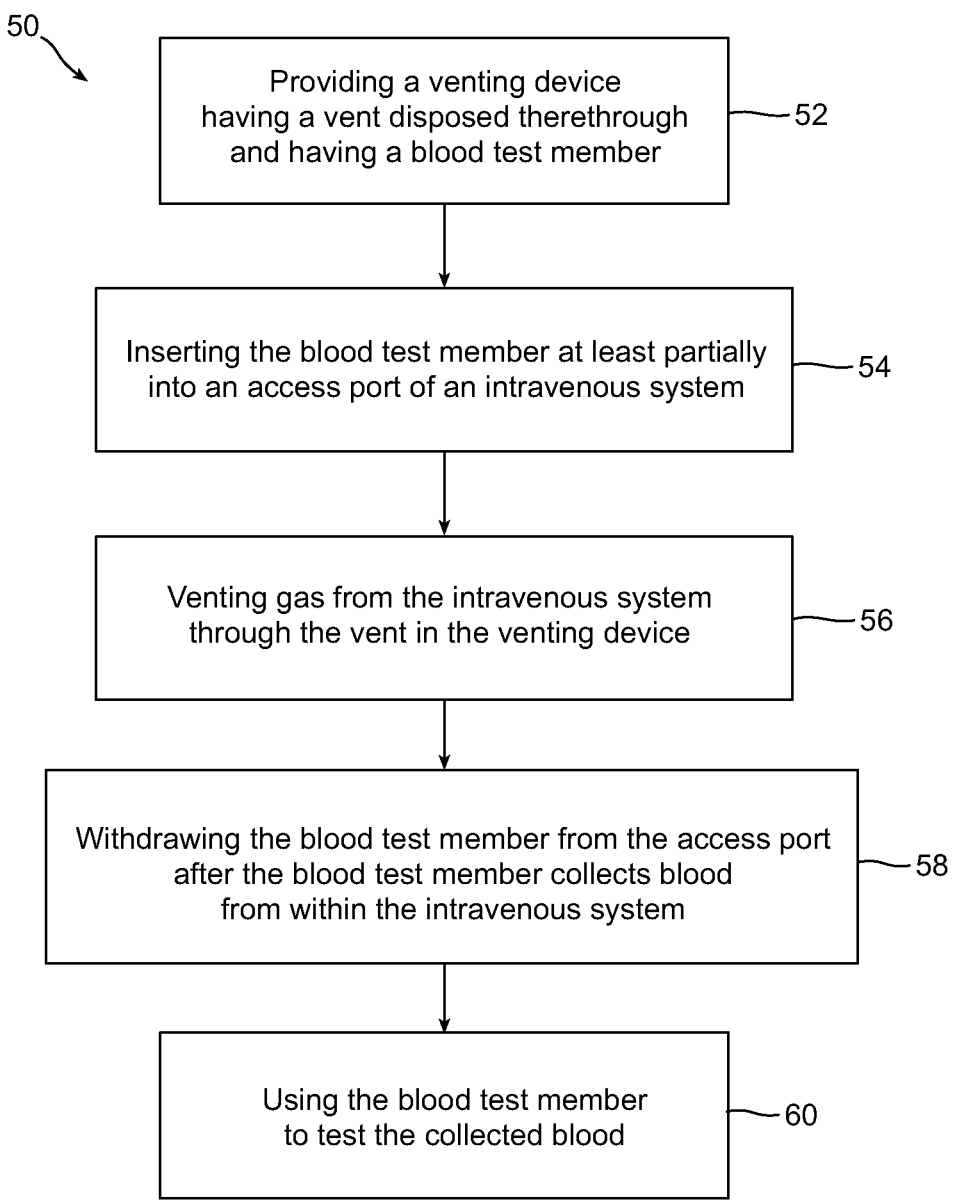
FIG. 4 is a flowchart of a method for venting a closed intravenous system and collecting blood therefrom, according to some embodiments.

FIG. 4 outlines a method 50 of gas venting and blood sampling that is at least partially illustrated in FIGS. 1-3, according to some implementations. This method 50 includes providing a venting device having a vent disposed therethrough and having a blood test member 52, as shown in FIG. 1. As shown in FIG. 2, the method includes inserting the blood test member at least partially into an access port of an intravenous system 54 and venting gas from the intravenous system through the vent in the venting device 56. Then, as shown in FIG. 3, the method 50 includes withdrawing the blood test member from the access port after the blood test member collects blood from within the intravenous system 58. The collected blood sample and blood test member can then be used to test the collected blood 60.

Figure 5:
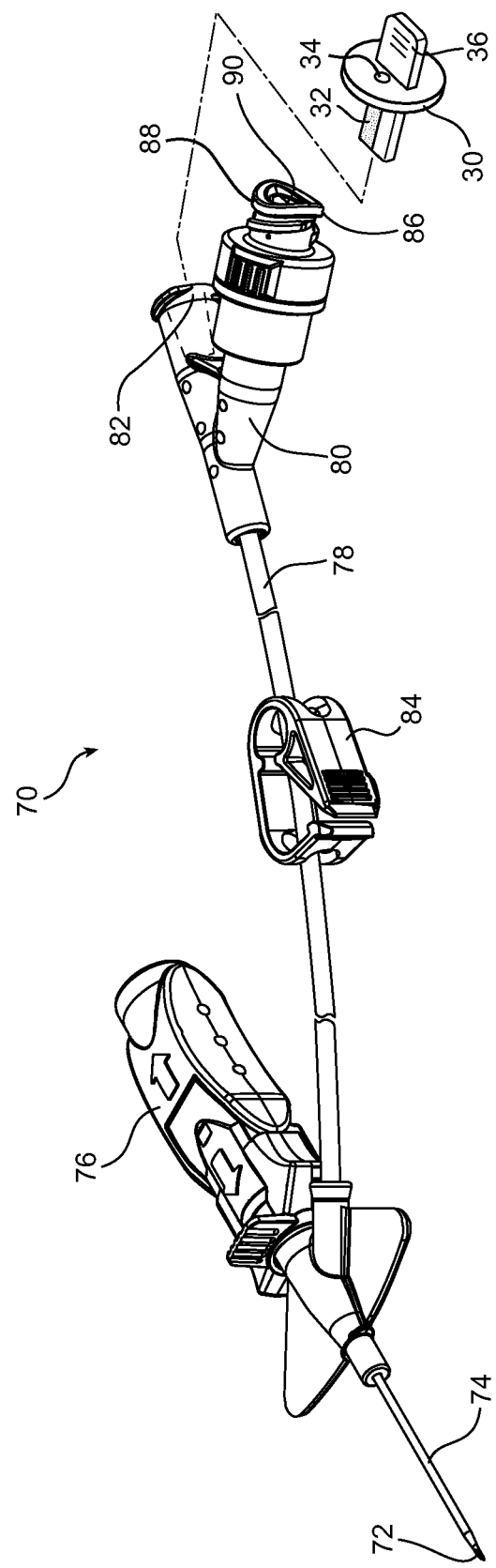
FIG. 5 is a perspective view of an IV catheter system having a venting device, according to some embodiments.

Additional aspects and embodiments of the blood test member and IV systems will now be described. Specifically, referring to FIG. 5, a closed IV (intravenous) catheter system 70, such as, for example, the BD NEXIVA™ Closed IV Catheter System, by Becton, Dickinson and Company, may be accessed using a venting device 30. In some embodiments, the system 70, as shown in FIG. 5, includes multiple vascular access devices such as an intravascular needle 72; an over-the-needle catheter 74 (such as a peripheral venous catheter); a catheter assembly 76; an integrated extension tubing 78 (also referred to as a catheter) with a Y adapter 80 having two ports 82 and clamp 84; and a Luer access device or port 86. Any adapter used to connect the integrated extension tubing 78 to another device may be used in place of the Y adapter 80. It will be understood that this system is representative of various closed IV systems that can incorporate a venting device 30, and a plurality of other IV system components can be included in such system.

During venting of the closed IV catheter system 70 blood flows from the patient, through the IV catheter system 70, into the access ports 82. Specifically, after the introducer needle 72 is withdrawn from the closed IV catheter system 70 both access ports 82 of the Y adapter 80 can be closed. A venting device 30 can be pre-installed in or later inserted into an access port 82 of the Y adapter 80. In some embodiments, a clamp 84 on the integrated extension tubing 78 may then selectively limit or eliminate blood flow one or more ports 82 and/or the venting device 30. As the clamp 84 opens the extension tubing 78 blood flows to the venting device 30 and forces air out the one or more vents 34 of the venting device 30 to the exterior environment. At this point, as explained with reference to FIG. 3, when the extension tubing 78 is vented and blood can be collected on the blood test member 32, to prevent additional blood flow, the clamp 84 may be closed when the venting device is removed.

As shown in FIG. 5, the venting device 30 has a distal body portion 33 that is shaped and sized for insertion into a Luer access port 86 having a septum 88 with a slit 90. In some embodiments, this distal body projection 33 alternatively or additionally is coupled to at least a portion of the blood test member 32. In some configurations, the distal body projection 33 supports the blood test member 32 is supported so that it can be inserted through a septum 90 of the Luer access port 86 without bending or breaking. In the illustrated configuration, the vents 32 of the venting device 30 can be disposed on or through either the blood test member 32 or the distal body projection 33.

In some embodiments, the venting device 30 has a distal body portion 33 that has an outer geometry that forms a press fit connection that closes off the open end of the open access port 82, permitting only gas to escape through the one or more vents 34. Accordingly, the distal portion of the venting device 30 can be shaped and sized for insertion into an open access port 82, such as that illustrated in FIG. 5. In these embodiments, the distal body portion 33 and/or the blood test member 32 have an outer geometry that approximates the inner geometry of the open access port 82.

As shown in FIG. 5, in some instances, a vent in the venting device 30 can comprise one or more holes 34 within the venting device 30. Alternatively, instead of holes 34, vents can comprise one or more channels formed along the exterior of the blood test member 32 or the distal body projection 33. In some instances, the venting device 30 can be inserted into a closed access port having a septum 88 with a slit 90 therein. When inserted through the slit 90 of the septum 88, small channels can remain at least partially open, forming a vent across the septum 88.

In some configurations, the dimensions of a vent hole or channel 34 are configured to allow air to pass through but not the more viscous blood. Furthermore, the total cross sectional area of a plurality of holes or channels 34 can be selected to permit enough air to pass therethrough without limiting the flow rate of blood flashback through the IV system 70 during the venting process. One having skill in the art will appreciate that the blood pressure of the patient is largely responsible for the rate at which air flow through the vents. As such, the flow rate through the system is affected by the combined effective hydraulic diameter of all flow paths.

Figure 7A:
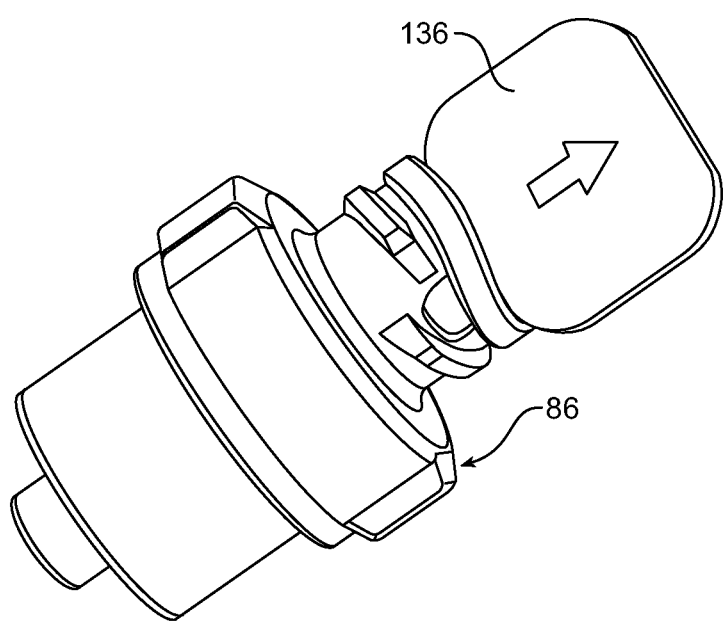
FIG. 7A is a perspective view of the venting device of FIG. 6 after it has been inserted within the luer access port.
Figure 7B:
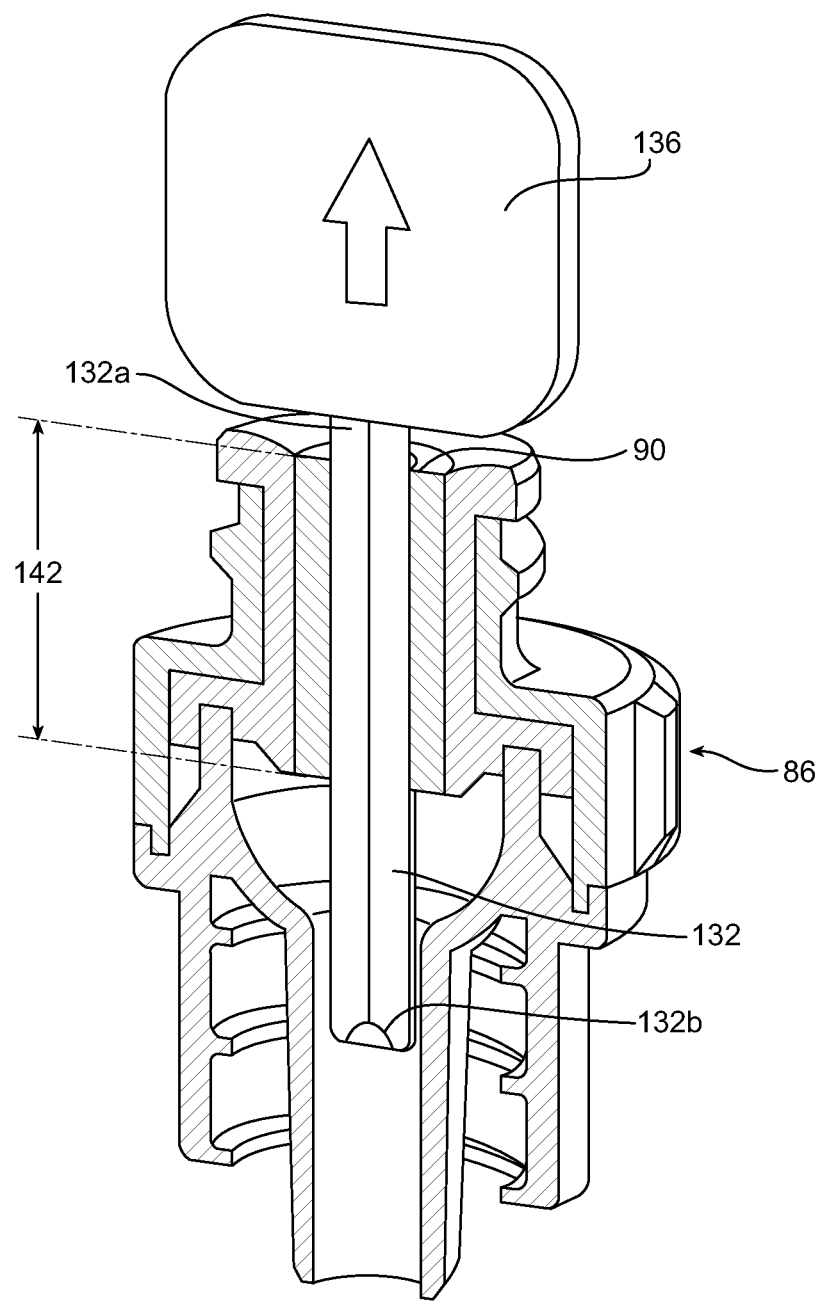
FIG. 7B is a cross-sectional view of the venting device of FIG. 7B within the luer access port.

FIGS. 6 through 7B depict a venting device 130 comprising a gripping tab 136 coupled to a blood test strip 132. The blood test strip 132 is shaped and sized to be selectively inserted and withdrawn from an access port 86. For instance, the blood test strip 130 can be configured to fit within the slit 90 of a septum 88 of the access port 86, as shown in FIGS. 7A-7B. As further shown, in some embodiments, the length 140 of the blood test strip 132 is longer than the thickness (the distance between the distal and proximal sides) of the septum 88 so that it spans the septum 88 when inserted therein. In some configurations, one or more vents 134 are disposed between the distal 132b and proximal 132a ends of the blood test strip 132 to vent air therebetween when the blood test strip 132 spans the septum 88. The one or more vents 134 can continue along or into the gripping tab 136 and end at a proximal, distal, side, or other portion of the gripping tab 136. These vents 134 can be holes or channels, as previously mentioned. FIG. 6 depicts a single channel 134 disposed on the outer surface of the blood test strip. In some embodiments, the vents 134 are holes or channels having a gas permeable membrane therein for permitting the passing of air, but not blood therethrough. In some embodiments, the one or more reservoirs are included in the blood test strip for collecting this blood sample. Such reservoirs can include an indent, a channel, a capillary tube, and/or an absorbent material. In some configurations, the one or more reservoir is configured to retain a minimum amount of blood when the blood test member 30 is withdrawn from the access port 28.

Figure 9B:
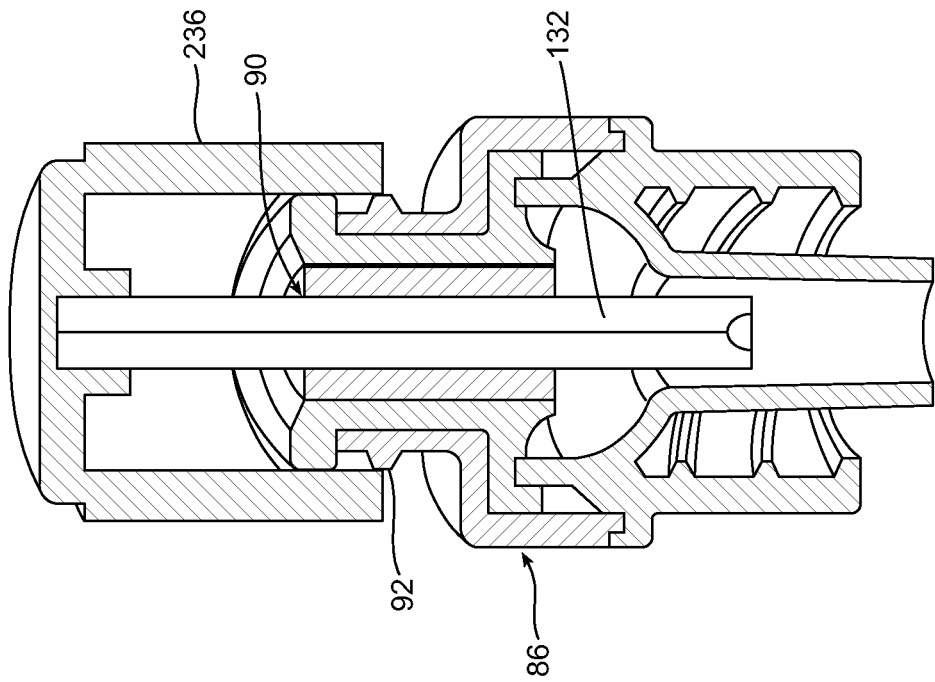
FIG. 9B is a cross-sectional view of the venting device of FIG. 9A within the luer access port.
Figure 9A:
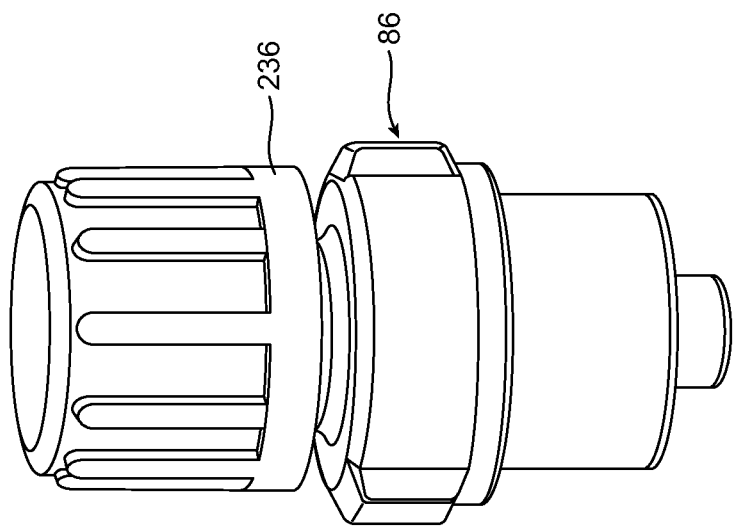
FIG. 9A is a perspective view of the venting device of FIG. 8 within the luer access port.

Like the venting device 130 of FIGS. 6 through 7B, the venting device 230 of FIGS. 8 through 9B include a blood test strip 132 extending distally from a gripping member. However, rather than a gripping tab 136, the gripping member is a cap 236. As shown in FIGS. 9A through 9B, the cap 236 can cover a part of the access port 86 and a part of the blood test strip 132. Such contact might contaminate the access port 86 or the blood test strip 132 or expose the clinician to the patient's blood. Accordingly, in some configurations, the cap 236 is shaped and sized to cover a portion of the access port 136 such as the septum 88 of the access port, and/or the Luer connecting portion of the access port 136. In some embodiments, the cap 236 couples to the access port 86. The cap 236 can include threads that coupled the cap to a Luer connector on an access port 82, 86. In other embodiments, the cap 236 snaps on and off an access port 82, 86. Still in other embodiments, the cap 236 slides on and off an access port 82, 86. Accordingly, the inner dimensions of the cap 236 can be slightly larger than the outer dimensions of an access port 82, 86.

FIGS. 10 through 11B depict a venting device 330 having a blood test member 132 and body 331 that is shaped and sized to fit within an open access port 82 to seal the opening view a press fit between the body 331 and the open access port 82. As illustrated, the body 331 has an outer geometry that is slightly smaller than the inner geometry of the access port 82. Accordingly, the body 331 can be selectively inserted into the access port and prevent blood from exiting out the access port 82. The venting device 330 of FIGS. 10 through 11B can have one or more vents disposed at various locations and on various parts thereof. For example, in some configurations, the one or more vents 334 are formed through the body 331 of the venting device, but not through the blood test member 132. In other embodiments, one or more vents are formed through the blood test member 132 and the body 331, such that the vent continues from the proximal end of the blood test member 132 into the body 331. As mentioned, these one or more vents can be holes, channels, or other such formations. When one or more vents are disposed through the body 331, the body can include a gas permeable membrane 338 that passes gases but not blood therethrough to prevent blood from exiting through the body 333.

As shown, the body 331 is elongated, such that the proximal portion of the body 331 forms the gripping member 336. In some embodiments, the gripping member 336 includes gripping features that facilitate gripping the surface of the gripping member 336. Such gripping features can include ridges, bumps, or other non-smooth surface features. Thus configured, the venting device 330 can effectively vent air from an IV system through an open access port 82.

In some embodiments, a venting device is pre-installed into an access port of an IV system, such that a clinician is not required to insert the venting device into the access port. This way, the IV system is prepared for immediate use, and can speed up the catheter insertion process, the venting process, and the blood sampling and testing processes. When the venting device is pre-installed the clinician does not need to clamp or unclamp the IV tubing prior to removing the venting device from the access port.

From the foregoing it will be seen that embodiments of a venting device may combine features that vent air, collect blood, and even directly test blood samples during the normal process of venous access. These embodiments facilitate the entire venting and blood sampling process for clinicians by reducing the number of process steps and reducing the amount of time between the insertion of an IV system and obtaining blood test results.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. A blood test strip comprising:
a blood test strip having a distal portion and a proximal portion, the distal portion being configured to be inserted into an access port of an intravenous catheter system;
one or more vents disposed between the distal portion and the proximal portion of the blood test strip, the one or more vents venting gas from within the intravenous catheter system while the distal portion of the blood test strip is inserted into the access port, the one or more vents further including at least one of a hole having dimensions that permits the passage of gas and prevents the passage of blood, a gas permeable membrane, and a channel formed on an outer surface of the blood test strip, the channel having dimensions that permits the passage of gas and prevents the passage of blood; and
a gripping member coupled to the proximal end of the blood test strip for removing the blood test strip from the access port.

2. The blood test strip of claim 1, wherein the one or more vents are further disposed through the gripping member.

3. The blood test strip of claim 1, wherein the gripping member is a cap that is shaped and sized to cover a female luer adapter of the access port.

4. The blood test strip of claim 1, wherein the gripping member is a gripping tab.

5. The blood test strip of claim 1, wherein the blood test strip includes at least one diagnostic reagent thereon.

6. The blood test strip of claim 3, wherein the cap includes threads that couple the cap to the female luer adapter.

7. The blood test strip of claim 1, wherein the gripping member is a cap having an inner diameter that is slightly larger than an outer diameter of the access port thereby allowing the cap to be press fit over the access port.

8. The blood test strip of claim 1, wherein the gripping member is a cap that covers the proximal portion of the blood test strip.

9. The blood test strip of claim 1, wherein the gripping member comprises a body having an outer diameter that is slightly smaller than an inner diameter of the access port thereby allowing the body to be press fit into the access port.

10. The blood test strip of claim 9, wherein the one or more vents extend from the proximal portion through the body.

11. The blood test strip of claim 1, wherein the distal portion is configured to extend through a septum of the access port when the distal portion is inserted into the access port.

12. The blood test strip of claim 1, wherein the one or more vents comprise one or more of holes, channels, indents, or capillary tubes.

13. The blood test strip of claim 12, wherein the one or more holes, channels, indents, or capillary tubes includes a gas permeable membrane.

14. The blood test strip of claim 1, wherein the blood test strip is pre-installed into the access port such that a clinician need not clamp or unclamp a tubing of the intravenous catheter system prior to removing the blood test strip from the access port.

* * * * *